(12) United States Patent
Macy et al.

(10) Patent No.: US 6,239,112 B1
(45) Date of Patent: *May 29, 2001

(54) WATER MISCIBLE MACROLIDE SOLUTIONS

(75) Inventors: Lowell R. Macy, Vermillion, SD (US); Raymond E. Hopponen, Fort Dodge, IA (US); Roger A. Wilson; James B. Williams, both of Lansdale, PA (US)

(73) Assignee: Merial, Inc., Athens, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/346,905

(22) Filed: Jul. 2, 1999

Related U.S. Application Data

(63) Continuation-in-part of application No. 09/112,690, filed on Jul. 9, 1998, now Pat. No. 5,958,888.

(51) Int. Cl.$^7$ .............................. A61K 31/70; C07H 1/00
(52) U.S. Cl. ................................. 514/29; 536/7.4
(58) Field of Search ................. 514/29; 536/7.4

(56) References Cited

U.S. PATENT DOCUMENTS 5,958,888 * 9/1999 Macy et al. ............................ 514/29

* cited by examiner

*Primary Examiner*—Elli Peselev
(74) *Attorney, Agent, or Firm*—Frommer, Lawrence & Haug LLP; William S. Frommer; Thomas J. Kowalski

(57) ABSTRACT

Water miscible pharmaceutical compositions containing up about 40% of a marcrolide such as an azalide antibiotic are prepared by reaction of the macrolide with acid in a non-aqueous water miscible organic solvent system.

19 Claims, No Drawings

WATER MISCIBLE MACROLIDE SOLUTIONS

RELATED APPLICATIONS

This application is a continuation-in-part of U.S. application Ser. No. 09/112,690, filed Jul. 9, 1998, now U.S. Pat. 5,958,888 allowed, which, as well as all documents cited herein and all documents cited in documents cited herein, are hereby incorporated herein by reference.

FIELD OF THE INVENTION

This invention relates to antibiotic compositions suitable for pharmaceutical use and in particular to water miscible solutions of macrolide antibiotics such as azalides.

BACKGROUND OF THE INVENTION

Macrolides, such as azalides, are a class of antibiotics which contain a many-membered lactone ring to which are attached one or more deoxy sugars. Macrolides are generally bacteriostatic, but have been shown to be bacteriocidal in high concentration against very susceptible organisms. Macrolides are most effective against gram-position cocci and bacilli, although they do possess some activity against some gram-negative organism. Macrolides exert their bacteriostatic activity by inhibiting bacterial protein synthesis by binding reversibly to the 50 S ribosomal subunit. ("Goodman & Gillman's the Pharmacological Basis of Therapeutics," 9th ed., J. G. Hadman & L. E. Limbird, eds., ch. 47, pp. 1135–1140, McGraw-Hill, New York (1996)).

The macrolides as a class are colorless and usually crystalline. Macrolides, such as azalides, are generally stable in near neutral solution, but they only have limited stability in acid or base solutions. The reason for this is because the glycosidic bonds hydrolyze in acid and the lactone ring saponifies in base ("Principles of Medicinal Chemistry," 2nd ed., W. F. Foye, ed., ch. 31, pp. 782–785, Lea & Febiger, Philadelphia (1981)). Hence, there is a need to prepare stable, water miscible pharmaceutical or veterinary compositions for parenteral, e.g., intravenous, intramuscular, subcutaneous, administration of macrolide antibiotics.

Macrolides as a class, which include azalides, are soluble in many organic solvents but are only slightly water soluble. Solutions of macrolides in organic solvent systems are used in human and veterinary practice for administration by the intramuscular and subcutaneous routes. These solutions cannot be used for intravenous administration because the macrolides precipitate when the solution is introduced into an aqueous medium as into body fluids. Aqueous solutions of salts of macrolides can be prepared but such solutions have such limited stability as to be limited to use for only a short time period after preparation.

A water miscible solution of macrolides, including azalides, which would be stable for an extended period of time would be of great value to both the medical and veterinary professions. It could be used for intravenous administration to rapidly provide therapeutic blood levels for more effective treatment of infectious diseases. A water miscible solution would also allow for more rapid absorption from intramuscular and subcutaneous injection sites leading to higher concentrations in body fluids and more effective control of infectious diseases. Such a solution would also be useful for oral administration to poultry and swine in their drinking water.

SUMMARY OF THE INVENTION

The present invention provides a stable, high potency water miscible formulation of macrolides, such as azalides. The macrolides as a class contain at least one basic nitrogen group which can be converted in non aqueous solutions into stable water miscible compositions by the addition of an acid. The resulting compositions are stable for extended periods of time and do not lead to precipitation of the macrolide, such as azalide, when introduced into an aqueous environment. The acid is added in an amount about equimolar to the number of available nitrogens present. Solutions containing as much as 40% of the macrolide, such as azalide can be prepared in this manner.

These and other embodiments are disclosed or are obvious from and encompassed by, the following Detailed Description.

DETAILED DESCRIPTION

Macrolides as a class include the erythromycin and its derivative as well as other derivatives such as the azalides. Erythromycin (MW 733.94 daltons) is the common name for a macrolide antibiotic produced by the growth of a strain of Streptomyces erythreous. It is a mixture of three erythromycins, A, B and C consisting largely of erythromycin A which is represented by the formula:

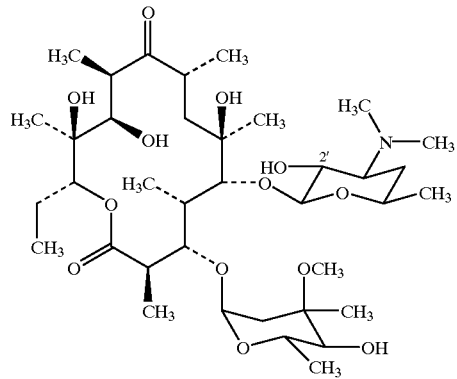

Its chemical name is (3R*,4S*,5S*,6R,7R*,9R*,11R*, 12R*, 13S*,14R*)-4-[(2,6-dideoxy-3-C-methyl-3-O-methyl-α-L-ribo-hexopyranosyl)-oxy]-14-ethyl-7,12,13-trihydroxy-3,5,7,9,11,13-hexamethyl-6[[3,4,6-trideoxy-3-(dimethylamino)-β-D-xylo-hexapyranosyl]oxy]oxacyclotetradecane-2,10-dione, $(C_{37}H_{67}NO_{13})$.

Erythromycin has a broad and essentially bacteriostatic action against many Gram-positive and some Gram-negative bacteria as well as other organisms including mycoplasmas, spirochetes, chlamydiae and rickettsiae. In humans, it finds usefulness in the treatment of a wide variety of infections. It finds wide application in veterinary practice in the treatment of infectious diseases such as pneumonias, mastitis, metritis, rhinitis, and bronchitis in cattle, swine and sheep.

Other derivatives of erythromycins include carbomycin, clarithromycin, josamycin, leucomycins, midecamycins, mikamycin, miokamycin, oleandomycin, pristinamycin, rokitamycin, rosaramicin, roxithromycin, spiramycin, tylosin, troleandomycin, and virginiamycin. As with the erythromycins, many of these derivatives exist as component mixtures. For example, carbomycin is a mixture of carbomycin A and carbomycin B. Leucomycin exists as a mixture of components $A_1$, $A_2$, $A_3$, $A_9$, $B_1$–$B_4$, U and V in various proportions. Component $A_3$ is also known as josamycin and leucomycin V is also known as miokomycin. The major components of the midecamycins is midecamycin A and the minor components are midecamycins $A_2$, $A_3$ and $A_4$. Likewise, mikamycin is a mixture of several components, mikamycin A and B. Mikamycin A is also known as virginiamycin $M_1$. Pristinamycin is composed of pristinamycins $I_A$, $I_B$, and $I_C$, which are identical to virginiamycins $B_2$, $B_{13}$ and $B_2$ respectively, and pristinamycin $II_A$ and $II_B$, which are identical to virginiamycin $M_1$ and 26,27-dihydrovirginiamycin $M_1$. Spiramycin consists of three components, spiromycin I, II, and III. Virginiamycin is composed of virginiamycin $S_1$ and virginiamycin $M_1$. All these components may be used in this invention. Sources of these macrolides are well known to the practitioner and are described in the literature in references such as "The Merck Index," 12th ed., S. Budarari, ed., Merck & Co., Inc., Whitehouse Station, N.J. (1996).

Azalides are semisynthetic macrolides antibiotics related to erythromycin A and exhibit similar solubility characteristics. This class includes compounds of the general structure

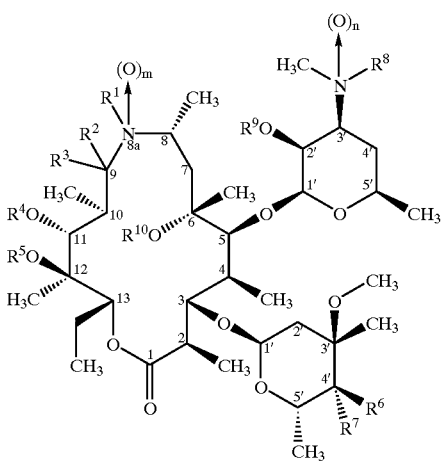

and the pharmaceutically acceptable salts and esters thereof, and the pharmaceutically acceptable metal complexes thereof, wherein $R^1$ is
  hydrogen,
  hydroxy;
  $C_{1-4}$ alkoxy;
  formyl;
  $C_{1-10}$ alkylcarbonyl, $C_{1-10}$ alkoxycarbonyl, aryloxycarbonyl, $C_{1-10}$ aralkoxycarbonyl, $C_{1-10}$ alkylsulfonyl, or arylsulfonyl wherein said $C_{1-10}$ alkyl group or aryl group is unsubstituted or substituted by 1–3 halo (F, Cl, Br), hydroxy, amino, $C_{1-5}$ acylamino or $C_{1-4}$ alkyl groups; or
  unsubstituted or substituted $C_{1-10}$ alkyl, $C_{2-10}$ alkenyl or $C_{2-10}$ alkynyl wherein said substituents are independently 1–3 of
    (a) aryl or heteroaryl optionally substituted by 1–3 halo (F, Cl, Br, I), $C_{1-4}$ alkyl, $C_{1-3}$ alkoxy, amino, $C_{1-4}$ alkylamino, di($C_{1-4}$ alkyl) amino or hydroxy,
    (b) heterocyclyl optionally substituted by hydroxy, amino, $C_{1-4}$ alkylamino, di($C_{1-4}$ alkyl)amino, $C_{1-4}$ alkylcarbonyloxy or $C_{1-4}$ alkylcarbonylamino,
    (c) halo (F, Cl, Br or I),
    (d) hydroxy optionally acylated by a group

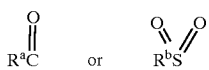

wherein
  $R^a$ is hydrogen, $C_{1-6}$ alkyl, aryl, heteroaryl, aralkyl, or heteroaralkyl and
  $R^b$ is $C_{1-6}$ alkyl or aryl,
    (e) $C_{1-10}$ alkoxy,
    (f) aryloxy or heterocaryloxy optionally substituted by 1–3 halo, hydroxy, amino or $C_{1-4}$ alkyl groups,
    (g) amino or $C_{1-10}$ alkylamino optionally acylated by a group

or $R^b SO_2$, wherein
  $R^a$ and
  $R^b$ are as defined above,
    (h) di($C_{1-10}$ alkyl)amino,
    (i) arylamino, heteroarylamino, aralkylamino or heteroarylakylamino wherein said aryl or heteroaryl group is optionally substituted by 1–3 halo, hydroxy, amino or $C_{1-4}$ alkyl groups,
    (j) mercapto,
    (k) $C_{1-10}$ alkylthio, alkylsulfinyl or alkylsulfonyl, arylthio, arylsulfinyl or arylsulfonyl wherein said aryl group is optionally substituted by 1–3 halo, hydroxy, amino or $C_{1-4}$ alkyl groups,
    (l) formyl,
    (m) $C_{1-10}$ alkylcarbonyl,
    (n) arylcarbonyl, heteroarylcarbonyl, aralkylcarbonyl or heteroarylalkylcarbonyl wherein said aryl or heteroaryl group is optionally substituted by 1–3 halo, hydroxy, amino or $C_{1-4}$ alkyl groups,
    (o) carboxy,
    (p) $C_{1-10}$ alkoxycarbonyl,
    (q) aryloxycarbonyl, heteroaryloxycarbonyl, aralkoxycarbonyl or heterozrylalkoxycarbonyl wherein said aryl or heteroaryl group is optionally substituted by 1–3 halo, hydroxy, amino or $C_{1-4}$ alkyl groups,
    (r) carbamoyl or sulfamoyl wherein the N-atom is optionally substituted by 1–2 $C_{1-6}$ alkyl groups or by a $C_{4-6}$ alkylene chain,
    (s) cyano,
    (t) isonitrilo,
    (u) nitro,
    (v) azido,
    (w) iminomethyl optionally substituted on nitrogen or carbon with $C_{1-10}$ alkyl,
    (x) oxo or
    (y) thiono;
  wherein said alkyl chain, if more than two carbons in length, can be optionally interrupted by 1–2 oxa, thia or aza (—NR—wherein R is hydrogen or $C_{1-3}$ alkyl) groups.

$R^{10}$ is hydrogen or
$R^1$ and $R^{10}$ together are $C_1$–$C_3$ alkylene optionally substituted by an oxo group;
$R^1$ and $R^4$ together are $C_1$–$C_3$ alkylene optionally substituted by an oxo group
$R^2$ and $R^3$ are hydrogen,
  $C_{1-10}$ alkyl,
  aryl
$R^2$ and $R^3$ together are
  oxo and
  thiono;
$R^4$ and $R^5$ are independently
  hydrogen and
  alkylcarbonyl;
$R^4$ and $R^5$ are together carbonyl;

$R^6$ and $R^7$ are both hydrogen or one of $R^6$ and $R^7$ is hydrogen and the other is hydroxy, an acyloxy derivative taken from the group consisting of formyloxy, $C_{1-10}$ alkylcarbonyloxy, arylcarbonyloxy and aralkylcarbonyloxy, or —$NHR^{12}$ wherein $R^{12}$ is hydrogen, arylsulfonyl or heteroarylsulfonyl optionally substituted by 1–3 halo or $C_{1-3}$ alkyl groups, alkylsulfonyl, or

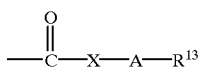

where

X is a connecting bond, O or NH,

A is a connecting bond or $C_1$–$C_3$ alkylene $R^{13}$ is hydrogen, $C_1$–$C_{10}$ alkyl, aryl, aralkyl, heteroaryl, heterocyclyl, or $C_3$–$C_7$ cycloalkyl, any of which $R^{13}$ groups other than hydrogen can be substituted by one or more of halogen, hydroxyl, $C_1$–$C_3$ alkoxy, cyano, isonitrilo, nitro, amino, mono- or di-($C_1$–$C_3$) alkylamino, mercapto, $C_1$–$C_3$ alkylthio, $C_1$–$C_3$ alkylsulfinyl, $C_1$–$C_3$ alkylsulfonyl, arylthio, arylsulfinyl, sulfamoyl, arylsulfonyl, carboxy, carbamoyl, $C_1$–$C_3$ alkylcarbonyl, or $C_1$–$C_3$ alkoxycarbonyl;

$R^6$ and $R^7$ are together oxo, hydroxyimino, alkoxyimino, aralkoxyimino or aminoimino;

$R^8$ is methyl, aralkoxycarbonyl, and arylsulfonyl;

$R^9$ is hydrogen, formyl, $C_{1-10}$ alkylcarbonyl, $C_{1-10}$ alkoxycarbonyl, and arylalkoxycarbonyl;

m and n are independently integers of zero or one; and said metal complex is taken from the group consisting of copper, zinc, cobalt, nickel and cadmium.

These compounds are disclosed in EP 568 699, herein incorporated by reference. Azalides as a class of components is well-known in the art and further derivatives are described, for example, in U.S. Pat. Nos. 5,869,629; 5,629,296; 5,434,140; 5,332,807; 5,250,518; 5,215,890; and 5,210,235, all incorporated herein by reference.

Particularly preferred is azithromycin. The structure of azithromycin is

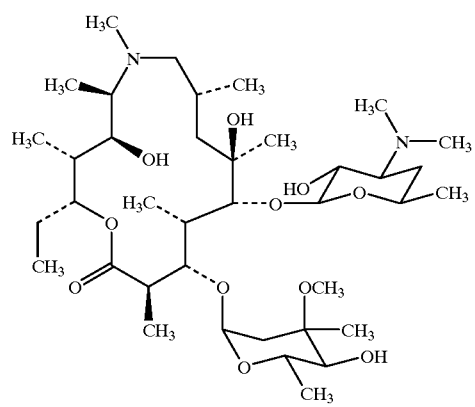

Compounds termed herein formula I and formula II have the following structures:

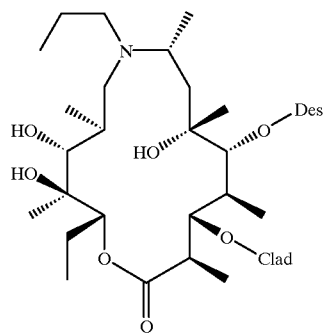

wherein Des is desosomine and Clad is cladinose (formula I) and

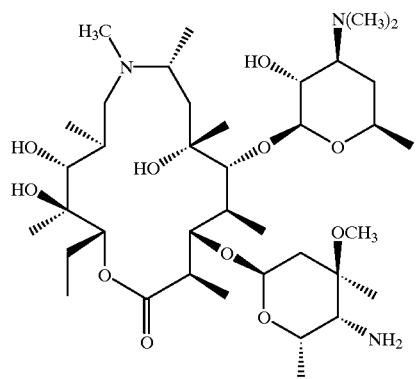

(formula II). The compound of formula II are also known as 8a-azalide. These compounds are disclosed in EP 508 699, herein incorporated by reference. The corresponding basic and acid addition salts and ester derivatives of the macrolides, including the azalides compounds, are also contemplated. These salts are formed from the corresponding organic or inorganic acids or bases. These derivatives include the customary hydrochloride and phosphate salts as well as the acetate, propionate and butyrate esters. These derivatives may have different names. For example, the phosphate salt of oleandomycin is matromycin and the triacetyl derivative is troleandomycin. Rokitamycin is leucomycin V 4-B-butanoate, 3B-propionate. When using these forms to prepare the inventive compositions, more or less acid may have to be added so that final amounts of acid in solution is approximately equal molar to the number of nitrogen atoms present in the molecule.

The term "acid" contemplates all pharmaceutically or veterinary acceptable inorganic or organic acids. Inorganic acids include mineral acids such as hydrohalic acids, such as hydrobromic and hydrochloric acids, sulfuric acids, phosphoric acids and nitric acids. Organic acids include all pharmaceutically or veterinary acceptable aliphatic, alicyclic and aromatic carboxylic acids, dicarboxylic acids tricarboxylic acids and fatty acids. Preferred acids are straight chain or branched, saturated or unsaturated $C_1$–$C_{20}$ aliphatic carboxylic acids, which are optionally substituted by halogen or by hydroxyl groups, or $C_6$–$C_{12}$ aromatic carboxylic acids. Examples of such acids are carbonic acid, formic acid, fumaric acid, acetic acid, propionic acid, isopropionic acid, valeric acid, α-hydroxy acids, such as glycolic acid and lactic acid, chloroacetic acid, benzoic acid, methane sulfonic acid, and salicylic acid. Examples of dicarboxylic acids include oxalic acid, malic acid, succinic acid, tataric acid and maleic acid. An example of a tricarboxylic acid is citric acid. Fatty acids include all pharmaceutically or veterinary acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

A variety of organic solvents or mixtures of solvents can be used as the vehicles for the compositions. The solvents contemplated are those water miscible organic solvents in which the macrolides are soluble and which are commonly acceptable in the pharmaceutical and veterinary fields to practitioners of those arts. Such compounds include alcohols, diols, triols, esters, amides, and ethers. Examples of suitable solvents that can be used include: methanol, ethanol, propanol, butanol, glycerol, propylene glycol; polyglycols such as polyethylene glycol 200, polyethylene glycol 300 and polyethylene glycol 400; pyrrolidones such as N-methyl pyrrolidone and 2-pyrrolidone; glycol ethers such as propylene glycol monomethyl ether, dipropylene glycol monomethyl ether and diethylene glycol ethyl ether. Other solvents include di(ethylene glycol)ethyl ether (transcutol), di(ethylene glycol)ethyl ether acetate, dimethyl isosorbide (Arlasolve DMI), di(propylene glycol)methyl ether (Dowanol DPM), di(propylene glycol)methyl ether acetate, glycerol formal, glycofurol, isopropylidene glycerol (Solketal), isopropyl myristate, N,N,-dimethyl acetamide, PEG 300, propylene glycol, and triacetin. Esters may also be used. Polar, aprotic solvents such as DMSO can also be used.

Antioxidants may be added to the composition of the present invention. Preferred antioxidants are those containing sodium. Especially preferred antioxidants include sodium bisulfite, monothioglycerol and sodium formaldehydesulfoxylate. Compositions of the present invention can be readily prepared by adding an amount of acid which is equal molar to the number of nitrogen groups present in the macrolide. For example, if there are three nitrogen groups, a total of approximately 2.7 to 3.3 moles of acid are used. Where there are two nitrogen groups present, a total of approximately 1.8 to 2.2 moles of acid is added. For erythromycin, which has one nitrogen group, a total of approximately 0.9 to 1.1 moles of acid is used. For example, when preparing a composition where erythromycin or a 8a-azalide is the macrolide, an acid such as acetic acid or succinic acid is first added in an amount about equimolar to the number of available nitrogens in the macrolide the selected organic solvent or solvents. Erythromycin or 8a-azalide is then added and the mixture stirred until complete solution results. One can also add all dry components to a container and then add the solvent or mixture of solvents while stirring. Other macrolides are prepared in a similar manner.

Thus, the invention relates to a stable water miscible a macrolide antibiotic composition comprising: a) a macrolide, such as an azalide, or a derivative thereof at a concentration of between about 10% and about 40% by weight, based on the volume of the composition; b) an acid present in an amount about equimolar to the number of available nitrogen groups present in the macrolide such as an azalide and forming a water soluble acetate compound of the macrolide to be formulated; and c) a water miscible non-aqueous vehicle composed of a suitable organic solvent or mixture of solvents.

Advantageously, the macrolide, such as an azalide or erythromycin is in the form of a base. Especially preferred is where the macrolide is 8a-azalide and where it is present in its base form.

The composition is advantageously provided in the form of a sterile injectable composition.

The macrolide preferably is present in a concentration of between about 7.5% and about 30%, more preferably above 7.5% to about 25% and most preferably about 10 to about 20% by weight based on the volume of the composition.

The vehicle advantageously is composed of propylene glycol monomethyl ether, or dipropylene glycol monomethyl ether, or diethylene glycol ethyl ether, or mixtures thereof. Advantageously, the vehicle is composed of N-methyl pyrrolidone, or glycerol formal or benzoyl benzoate in a concentration of between about 30% and about 50% by volume and the balance is propylene glycol. Also, the vehicle can be composed of N-methyl pyrrolidone or glycerol formal in a concentration of between about 30% and about 50% by volume and the balance is polyethylene glycol 200, or polyethylene glycol 300 or polyethylene glycol 400.

The invention especially relates to a stable water miscible 8a-azalide composition comprising: a) 8a-azalide at a concentration of between about 10% and about 20% by weight, based on the volume of the composition; b) succinic acid present in an amount between about 1.1 and about 1.5% and forming a water soluble succinate compound of azalide; and c) a water miscible non-aqueous vehicle composed of a suitable organic solvent or mixture of solvents.

The invention further relates to a method of preparing a stable, high potency water miscible macrolide antibiotic composition comprising the steps of: a) preparing a non-aqueous vehicle of a water miscible organic solvent or solvents; b) adding the acid to the macrolide, such as an azalide, so that the total concentration of acid is approximately equal molar to the number of free nitrogen groups present in the macrolide with respect to the desired concentration of the macrolide; and c) combining the acid solution with the macrolide in order to achieve a final concentration of between about 7.5% at 40% weight of the macrolide. Alternatively, the inventive composition may be prepared by a method comprising the steps of: a) adding the acid to the marcolide, such as azalide, in an amount so that the total concentration of acid is approximately equal molar to the number of free nitrogen groups present in the macrolide with respect to the desired concentration of the macrolide; b) preparing a non-aqueous vehicle of a water miscible organic solvent or solvents; and c) combining the acid solution with the mixture of acid and macrolide in order to achieve a final concentration of between about 7.5% and about 40% by weight of the macrolide.

A better understanding of the present invention and of its many advantages will be had from the following example, given by way of illustration.

EXAMPLE 1

One liter of a 20% solution of erythromycin was prepared according to the following procedure:

| Erythromycin (based on a potency of 910 micrograms per milligram) | |
|---|---|
| 200 g/0.910 = | 219.8 g |
| Glacial acetic acid | 16.4 g |
| N-methyl pyrrolidone | 400.0 mL |
| Propylene glycol | qs 1000.0 mL |

The glacial acetic acid was added to a mixture of the N-methyl pyrrolidone and 300 mL of propylene glycol and mixed. The erythromycin was added slowly with stirring. When the erythromycin was completely dissolved, the solution was brought to volume with propylene glycol.

EXAMPLE 2

Short-term Stability Study

The following 8a-azalide formulation was prepared by placing the dry ingredients into a suitable container, and adding the liquids, while stirring. Stirring was continued until a clear solution was obtained. The composition of the formulation was as follows:

| | |
|---|---|
| 8a-azalide | 12.5% w/v |
| succinic acid | 1.3% w/v |
| sodium bisulfite | 0.5% w/v |
| 40/60% v/v mixture of glycerol formula/ propylene glycol | q.s. AD 100% w/v |

The short-term stability of the formulation was then tested by storing the formulation at 50° C. for eight weeks. No significant changes to the formulation, which remained clear, were observed.

The above description of the invention is intended to be illustrative and not limiting. Various changes or modification in the embodiment described may occur to those skilled in the art. These can be made without departing from the scope or spirit of the invention.

Having thus described in detail preferred embodiment of the present invention, it is to be understood that the invention defined by the appended claims is not to be limited by particular details set forth in the above description as many apparent variations therefore are possible without departing form the spirit or scope thereof.

What is claimed is:

1. A stable water miscible azalide antibiotic composition comprising:

a) an azalide macrolide antibiotic or a derivative thereof at a concentration of between about 7.5% and about 40% by weight, based on the volume of the composition;

b) an acid present in an amount about equimolar to the number of available nitrogen groups present in the azalide and forming a water soluble salt compound of the azalide; and c) a water miscible non-aqueous vehicle composed of a veterinary or pharmaceutically acceptable organic solvent or mixture of solvents.

2. A composition according to claim 1 wherein the azalide is azithromycin, formula I or formula II, said formula I being

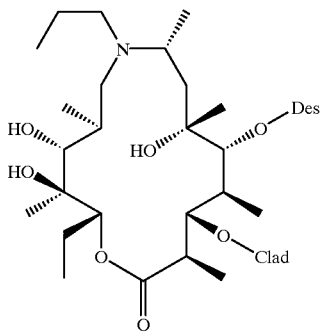

wherein Des is desosomine and Clad is cladinose in said formula I, and said formula II being

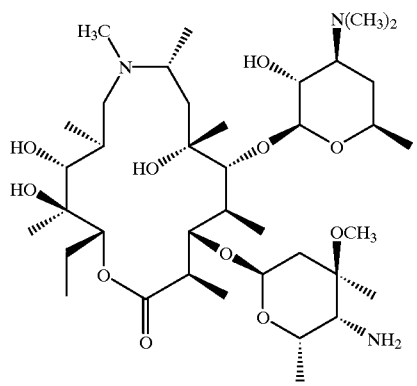

3. A composition according to claim 2 wherein the macrolide antibiotic is 8a-azalide.

4. A composition according to claim 2 wherein the macrolide antibiotic is formula I or azithromycin, said formula I being

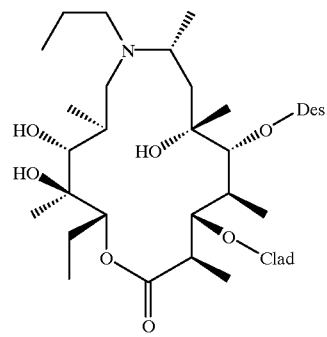

wherein Des is desosomine and Clad is cladinose in said formula I.

5. A composition according to claim 1 wherein the azalide is in the form of a base.

6. A composition according to claim 1 wherein the composition is provided in the form of a sterile injectable composition.

7. A composition according to claim 1 wherein the macrolide antibiotic is present in a concentration of between about 7.5% and about 20% by weight based on the volume of the composition.

8. A composition according to claim 1 wherein the vehicle is composed of propylene glycol monomethyl ether, or dipropylene glycol monomethyl ether, or diethylene glycol ethyl ether, or mixtures thereof.

9. A composition according to claim 1 wherein the vehicle is composed of N-methyl pyrrolidone or glycerol formal in a concentration of between about 30% and about 50% by volume and the balance is propylene glycol.

10. A composition according to claim 1 wherein the vehicle is composed of N-methyl pyrrolidone or glycerol formal in a concentration of between about 30% and about 50% by volume and the balance is polyethylene glycol 200, or polyethylene glycol 300 or polyethylene glycol 400.

11. A composition according to claim 1, wherein the acid is selected from the group consisting of acetic acid, propionic acid, isopropionic acid, butyric acid, iso-butyric acid, sec-butyric acid, and valeric acid.

12. A composition according to claim 1, wherein the acid is succinic acid.

13. A composition according to claim 1, which further comprises an antioxidant.

14. A composition according to claim 13, where the antioxidant is selected from the group consisting of sodium bisulfite, monothioglycerol, and sodium formaldehydesulfoxylate.

15. A stable water miscible azalide antibiotic composition comprising:

a) formula I, formula II or azithromycin at a concentration of between about 7.5% and about 40% by weight, based on the volume of the composition, said formula I being

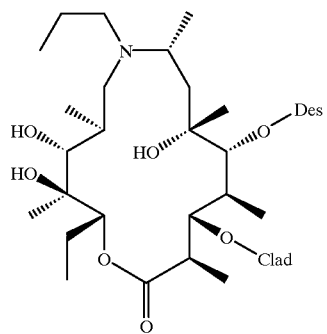

wherein Des is desosomine and Clad is cladinose in said formula I, and said formula II being

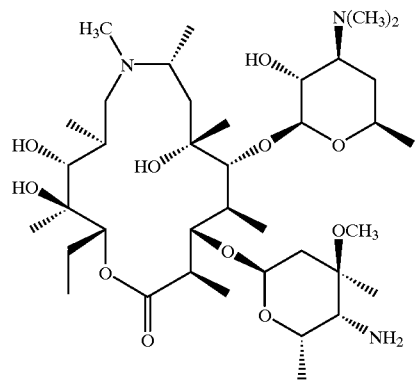

b) acetic or succinic acid present in an amount at least equimolar to the number of free nitrogen atoms present in the azalide and forming a water soluble acetate or succinic compound of the azalide; and c) a water miscible non-aqueous vehicle composed of a suitable organic solvent or mixture of solvents.

16. A composition according to claim 15, wherein the antibiotic is at a concentration of about 10 to about 20%.

17. A composition according to claim 15, wherein the macrolide is 8a-azalide, the acid is succinic acid, the water miscible non-aqueous vehicle is glycerol formal in propylene glycol, and which further comprises sodium bisulfite.

18. A method of preparing a stable, high potency water miscible azalide antibiotic composition comprising the steps of:

a) preparing a non-aqueous vehicle of a water miscible organic solvent or solvents;

b) mixing acid with azalide in a concentration so that the total amount of acid is equimolar to the number of free nitrogen groups present in the azalide with respect to the desired concentration of the azalide; and c) combining the acid solution to the mixture in order to achieve a final concentration of between about 7.5% and about 40% by weight of the macrolide.

19. The method according to claim 18, wherein the azalide antibiotic is formula I, formula II or azithromycin and the acid is acetic or succinic acid, said formula I being

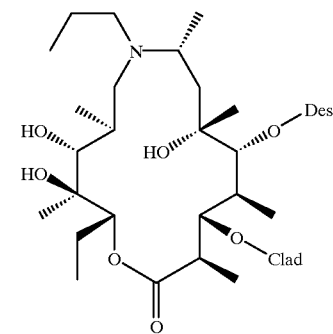

wherein Des is desosomine and Clad is cladinose in said formula I, and said formula II being

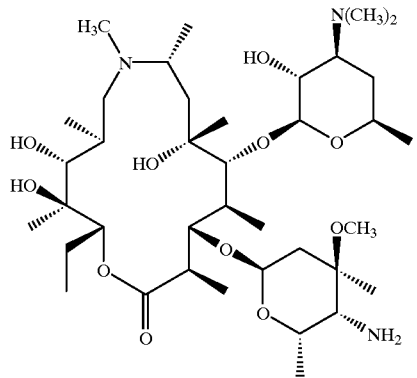

* * * * *